(12) United States Patent
Vervoort et al.

(10) Patent No.: US 7,026,112 B1
(45) Date of Patent: Apr. 11, 2006

(54) OLIGONUCLEOTIDES FOR THE AMPLIFICATION AND DETECTION OF EPSTEIN BARR VIRUS (EBV) NUCLEIC ACID

(75) Inventors: Marcel Bartolina Hendrikus Johannes Vervoort, Amsterdam (NL); Adrianus Johannes Christiaan van den Brule, Diemen (NL); Jaap Michiel Middeldorp, Oss (NL)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 09/623,329

(22) PCT Filed: Mar. 1, 1999

(86) PCT No.: PCT/EP99/01392

§ 371 (c)(1),
(2), (4) Date: Nov. 13, 2000

(87) PCT Pub. No.: WO99/45155

PCT Pub. Date: Sep. 10, 1999

(30) Foreign Application Priority Data

Mar. 4, 1998 (EP) ............................................. 98200655
Dec. 14, 1998 (EP) ............................................. 98204231

(51) Int. Cl.
*C12Q 1/68* (2006.01)
*C12P 19/34* (2006.01)
*C07H 21/04* (2006.01)
*C07H 21/02* (2006.01)

(52) U.S. Cl. ............................... 435/5; 435/6; 435/91.2; 536/23.1; 536/23.73; 536/24.32; 536/24.33

(58) Field of Classification Search ...................... 435/5, 435/6, 91.2; 536/23.1, 23.72, 24.32, 24.33
See application file for complete search history.

(56) References Cited

U.S. PATENT DOCUMENTS 4,965,188 A * 10/1990 Mullis et al. .................. 435/6

FOREIGN PATENT DOCUMENTS

| DE | 196 27 932 A1 | 1/1998 |
|---|---|---|
| EP | 0 316 170 A2 | 5/1989 |
| EP | 0 574 048 A2 | 12/1993 |
| EP | 0 628 568 A2 | 12/1994 |
| JP | 05 309000 A | 11/1993 |
| WO | WO 93/07882 | 4/1993 |
| WO | WO 93/11267 | 6/1993 |
| WO | WO 93/23569 | 11/1993 |
| WO | WO 95/03415 | 2/1995 |
| WO | WO 97/32036 | 9/1997 |
| WO | WO 97/37669 | 10/1997 |
| WO | WO 98/04746 | 2/1998 |

OTHER PUBLICATIONS

Myers, R.M. 1996. GenBank Accession No. G29936.*
Myers, R.M.. 1996. GenBank Accession No. G34340.*
NCBI, National Library of Medicine, NIH (Bethesda, MD, USA) Accession No. M80517, Apr. 1996.*
NCBI Database, National Center for Biotechnology Information, National Library of Medicine, NIH (Bethesda, MD, USA) Accession No. I U21195, May 24, 1995.*
Cheung et al., "Detection of Viral Sequences by Internally Calibrated Gene Amplification," Biotechniques, vol. 14, No. 5, 1993, pp. 785–789.
Patent Abstracts of Japan, vol. 018, No. 114, 1994.
Kievits et al., "NASBA™ Isothermal Enzymatic in vitro Nucleic Acid Amplification Optimized for the Diagnosis of HIV–1 Infection," Journal of Virological Methods, vol. 35, No. 3, 1991, pp. 273–286.
Database NCBI [online], "Human Herpesvirus 4 Genome," Accession: NC001345, 1983 (abstract only).
Zhang et al., "Transcriptional Expression of the Viral Genome in the Epstein–Barr Virus–Induced Tamarin Lymphoma and the Corresponding Lymphoblastoid Tumour Lines," Virus Research, vol. 26, 1992, pp. 153–166.
Tierney et al., "Epstein–Barr Virus Latency in Blood Mononuclear Cells: Analysis of Viral Gene Transcription During Primary Infection and in the Carrier State," Journal of Virology, vol. 68, No. 11, 1994, pp. 7374–7385.
Brooks et al., "Epstein–Barr Virus Latent Gene Transcription in Nasopharyngeal Carcinoma Cells: Coexpression of EBNA1, LMP1 and LMP2 Transcripts," Journal of Virology, vol. 66, No. 5, 1992, pp. 2689–2697.
Brink et al., Multiprimed cDNA Synthesis Followed by PCR is the Most Suitable Method for Epstein–Barr Virus Transcript Analysis in Small Lymphoma Biopsies, Mol. Cell. Probes, vol. 11, 1997, pp. 39–47.

(Continued)

*Primary Examiner*—Carla J. Myers
(74) *Attorney, Agent, or Firm*—Myers Bigel Sibley & Sajovec, P.A.

(57) ABSTRACT

The present invention is concerned with oligonucleotides that can be used as in the amplification and detection of Epstein Barr Virus (EBV) nucleic acid, in particular RNA-specific sequences. Furthermore a method for the diagnosis of EBV associated malignant and non-malignant diseases is provided. The oligonucleotides according to the present invention are specifically suited for the detection of EBV gene expression in circulating peripheral blood cells, in human (tumor) tissue samples and thin sections thereof using "in solution" amplification or "in situ" amplification techniques and in other biological samples potentially containing EBV-infected cells.

5 Claims, 11 Drawing Sheets

(2 of 11 Drawing Sheet(s) Filed in Color)

OTHER PUBLICATIONS

Wei et al., "Expression and Tumorigenicity of the Epstein–Barr Virus BARF1 Gene in Human Louckes B–Lymphocyte Cell Line," Cancer Research, vol. 54, 1994, pp. 1843–1848.

Touitou et al., "Transcriptional Analysis of the Epstein–Barr Virus Interleukin 10 Lomologue During the Lytic Cycle," Journal of General Virology, vol. 77, 1996, pp. 1163–1168.

Labrecque et al., "Epstein–Barr Virus in Epithelial Cell Tumors: A Breast Cancer Study," Cancer Research, vol. 55, 1995, pp. 39–45.

Brink et al., "Nucleic Acid Sequence–Based Amplification, A New Method for Analysis of Spliced and Unspliced Epstein–Barr Virus Latent Transcripts, and its Comparison with Reverse Transcriptase," Journal of Clinical Microbiology, vol. 36, No. 11, 1998, pp. 3164–3169.

Hayes et al., "Expression of Epstein–Barr Virus (EBV) Transcripts Encoding Homologues to Important Human Proteins in Diverse EBV Associated Diseases," Molecular Pathology, vol. 52, No. 2, 1999, pp. 97–103.

* cited by examiner

Figure 3C:

vIL-10 (BCRF1) NASBA
variations in Betain concentration

OLIGONUCLEOTIDES FOR THE AMPLIFICATION AND DETECTION OF EPSTEIN BARR VIRUS (EBV) NUCLEIC ACID

The present invention is concerned with oligonucleotides that can be used in the amplification and detection of Epstein Barr Virus (EBV) mRNA. Furthermore a method for the diagnosis of EBV associated malignant and non-malignant diseases is provided.

The oligonucleotides according to the present invention are specifically suited for the detection of EBV gene expression in circulating peripheral blood cells, in human (tumor) tissue samples and thin sections thereof using "in solution" amplification or "in situ" amplification techniques and in other biological samples potentially containing EBV-infected cells.

GENERAL BACKGROUND

Epstein-Barr Virus (EBV) is an ubiquitous human herpes virus that was first discovered in association with the African (endemic or e) form of Burkitt's lymphoma (BL). Subsequently the virus was also found associated with nasopharyngeal carcinoma (NPC) and was shown to be the causative agent of infectious mononucleosis (IM). Infection usually occurs during early childhood, generally resulting in a subclinical manifestation, occasionally with mild symptoms. Infection during adolescence or adulthood, however, can give rise to IM characterized by the presence of atypical lymphocytes in the periphery. The bulk of these lymphocytes are T lymphocytes; however, included in their number are a small population of B lymphocytes infected by EBV. The infection of B lymphocytes may also be accomplished in vitro. Such cells become transformed and proliferate indefinitely in culture and have been referred to as "immortalized", "latently infected" or "growth transformed". As far as is known, all individuals who become infected with EBV remain latently infected for life. This is reflected by the lifelong continuous presence of small numbers of EBV-genome positive transformed B-cells among the circulating peripheral blood lymphocytes and the continuous but periodic shedding of virus In the oropharynx.

In the vast majority of cases EBV infection results in a lynmphoproliferative disease that may be temporarily debilitating, but is always benign and self-limiting. In certain immunosuppressed individuals, however, the result can be uncontrolled lymphoproliferation leading to full-blown malignancy. This occurs in individuals who are immunosuppressed intentionally, particularly children receiving organ transplants who are treated with cyclosporine A, or opportunistically, as in the case with individuals infected with HIV, or genetically, as in the case of affected males carrying the XLP (x-linked lymphoproliferative syndrome) gene. In these cases the resulting malignancies derive from the polyclonal proliferation of EBV-infected B cells. In addition, in such patients uncontrolled epithelial replication of the virus is detectable in lesions of oral hairy leukoplakia. Thus, the immune response plays a central role in the control of EBV infection.

Epstein Barr virus gene expression and molecular diagnostic approaches.

For many years Burkitt's lymphoma (BL) derived cell lines and EBV-transformed peripheral blood B-cells, also named lymphoblastoid cell lines (LCL) were considered to be the prototype model system for studying EBV-mediated transformation and oncogenesis.

During the last few years the entire DNA sequence of prototype virus strain, B95-8, has been determined. Analysis of this sequence has resulted in the identification of more than 80 open reading frames (Baer et al., Nature 310; 207–211 (1984)). The nomenclature for EBV reading frames is based on their position in the virus genome. The names begins with the initials of the BamH1 or EcoR1 restriction fragment where expression begins. The third character in the name if L or R, depending on whether the expression is leftward or rightward on the standard map. (so BLLF2 is the second leftward reading frame starting in BamH1 restriction fragment L.).

Basically three different gene transcription patterns have been observed in the various EBV-associated malignancies. These patterns are called latency type I, type II and type III, although recent data show the presence of additional transcripts complicating this typing system. Latency type I is characterized by the expression of Epstein Barr Nuclear Antigen 1 (EBNA-1; BKRF1) and the small non-coding RNA's Epstein Barr Early RNA 1 and 2 (EBER-1 and EBER-2). More recently a novel set of transcripts (BAFR0), with potential protein coding capacity in a number of small open reading frames included within these transcripts, has been found in all cells expressing the latency type I pattern. Latency type II is characterised by the expression of Latent Membrane Protein 1 (LMP-1; BNLF1) and LMP-2A/-2B (BNRF1), in addition to the type I transcripts mentioned above. LMP2 transcripts can only be expressed when the viral genome is in the covalently dosed circular form as these transcripts cross the terminal repeats on the viral genome and cannot be formed when the viral genome is in its linear "lytic" state. Latency type III is characterised by the expression of the nuclear antigens EBNA-2, EBNA-3A, EBNA-3B, EBNA-3C and EBNA-4 (also referred to as EBNA-2, -3, -4, -6 and -5 respectively), in addition to the type II program transcripts. The expression of the different latency-associated transcription programs is influenced by host cell parameters, such as the level of methylation and cellular differentiation. As a consequence, EBV-gene expression can be observed to initiate from different promoter sites, depending upon the methylation state of the viral genome.

The association of expression of different latency type viral transcription profiles with the various EBV-associated malignancies has been determined in recent years mainly by means of Reverse-Transcripase Polymerase Chain Reaction (RT-PCR) analysis of RNA derived from tumor biopsy specimens or by analysis of cDNA libraries made from polyadenylated mRNA, selectively isolated from tumor tissue or in vitro (including in xenografted (nude) mice) propagated tumor cell lines and LCL's. Using these types of analysis, type I latency is found in BL tumor cells in vivo and sporadic BL cell lines in vitro. Type II latency is found in NPC, EBV-positive cases of Hodgkin's Lymphoma, T-cell, NK-cell and sporadic B-cell non-Hodgkin lymphoma (T-/NK-/B-NHL) and thymic and parotid carcinomas in the immunocompetent host, whereas type III latency patterns are found in most BL and LCL lines maintained in vitro and in pre-malignant lymphoproliferations and immunoblastic lymphoma which are observed mainly in immunocompromised individuals. In the latter populations sporadic lyomyosarcoma is also found which may express the type II pattern, whereas gastric carcinomas in non-compromised patients were found to express rather a type I latency pattern. There is sill no consensus on the exact transcription pattern of the truly latently infected B-cell that can be detected in the healthy EBV carrier. Depending on the method used for isolation of these latently infected B-cells, EBNA-1, EBER's and LMP-2 transcripts have been found, but also patterns including only EBNA-1 or only EBER's plus LMP-2 have been described.

It should be realised that these different patterns of viral (latent) gene transcription in B-cells and tumor tissue actually represents transcription in "bulk" (tumor) material and do not necessary reflect the expression pattern of each individual (tumor) cell. By immunohistochemical (IH) analysis of thin sections of various EBV-associated tumors using monoclonal antibodies to defined EBV latency-associated gene products, such as EBNA-1, EBNA-2 and LMP-1, a different picture is emerging. In recent studies using IH methodology it was found that the majority of tumor cells in AIDS and in post-transplant associated immunoblastic lymphoma display a pattern consistent with latency type I (only EBER-1/-2 and EBNA-1 detectable), whereas a minority express either latency type II (EBNA-1 plus LMP-1) or a novel form of latency characterised by the co-expression of EBNA-1 and EBNA-2 (Oudejans et al., Am. J. Pathol. 147 (1995) 923–933). Only rarely cells were observed that co-express EBNA-2 and LMP-1 which would be indicative for Latency type III. This could mean that the classic picture of viral gene expression associated with the different EBV-linked malignant diseases has to be revised to incorporate these more detailed findings.

In fact an even more differentiated picture is emerging as dearly different EBV-encoded genes are found to be expressed in different EBV-associated malignancies. Occasionally, viral gene products previously considered to belong to the (early) lytic phase of the viral life cycle are detectable, probably derived from occasional tumor cells switching to lytic viral replication under influence of local influences. This phenomenon can be clearly observed in nasopharyngeal carcinoma (NPC) where the switch to lytic replication in small nests of tumor cells is associated with cellular differentiation as revealed by the formation of cytokeratin filaments. Alternatively, such lytic gene products may derive from tumor infiltrating and differentiating B-cells carrying latent viral genomes, or from local endothelial and specialized epithelial cells that may become productively infected by EBV.

In addition to the latency-associated gene products and gene-expression clearly linked to local lytic viral replication, some viral genes usually considered to belong to the set of EBV early genes have been found to be expressed in selected EBV-associated tumors. These genes include viral homologues of cellular genes that may have a function in the pathogenesis of certain EBV-malignancies; e.g. BHRF1, the human Bcl-2 homologue providing apoptosis resistance and found to be expressed almost exclusively in B-NHL, or BARF1, a homologue of cellular ICAM-1, expressed in NPC and OHL but not in HD and other lymphoma, or BCRF1, the viral homologue of human IL-10 which may confer local immunomodulating activity mainly found in immunoblastic lymphoma in immunocompromised patients, or BDLF2, which has some homology to cellular cydin B1 and may function on overriding normal cell cycle control.

Furthermore, genes that effectively mediate the switch from latent to lytic cycle gene expression in vitro can be found to be expressed in vivo without detectable full lytic cycle induction, a situation referred to as restricted or abortive lytic gene expression.

Therefore, at the single cell level, EBV gene expression is not homogeneously distributed throughout the tumor and different tumor cell populations may express (slightly) different patterns of EBV genes. Thus, in addition to analysing EBV gene expression in nucleic acid extracts prepared from whole tumor biopsy samples, information on viral gene expression at the single cell level is required to accurately describe the transcriptional activity of the EBV genome in the tumor cells.

It has been suggested that the switch to lytic gene expression may be positively related to success of therapy, as such cells are less resistant to apoptosis and are more immunogenic, thus being more sensitive to drug/radiation therapy and host (immune) surveillance and repair mechanisms. Thus, in addition to analysing the latency associated gene transcripts, accurate detection and relative quantitation of EBV-encoded viral lytic gene products in the tumor is of diagnostic and prognostic relevance.

In addition to its use in specific diagnosis and monitoring of the EBV-associated malignancies as described above, analysis of viral gene expression may be of relevance in differential diagnosis of oral hairy leukoplakia, which is characterised by expression of viral lytic genes in the absence of detectable EBNA-1 and EBER expression and for diagnosing acute and chronic/persistent B-cell lymphoproliferations which may have a self-limiting or non-malignant progression.

All these findings point to the relevance of accurate determination of type and level of viral gene expression for diagnosis of EBV-associated malignancies and pre-malignant lymphoproliferations.

In addition to or instead of analysis of viral gene expression in tumor or otherwise affected tissue specimens, detection and quantitation of virus infected (tumor) cells in the circulation and analysis of viral gene expression in these cells may provide a more accessible means of molecular diagnosis, not only applicable for detection of circulating tumor cells in already affected patients or for pre-emptive screening purposes in patients at risk, such as post-transplant- and AIDS-patients and otherwise immuno-compromised individuals, but also relevant for monitoring the effect(s) of anti-tumor therapy.

Besides measuring of the EBV-associated tumor load, which may be achieved by quantitating the level of viral DNA in a particular patient specimen, the qualitative and quantitative analysis of viral gene transcription is essential for differential diagnosis and prognosis and may be relevant for determining therapeutic intervention strategies.

Molecular analysis using either nucleic acid or immunologic reagents requires detailed knowledge of the target molecules involved, especially regarding strain/epitope variation. Selection of gene segments and epitopes that are highly conserved among different EBV-strains and isolates is of crucial importance for design and development of diagnostic reagents that can be applied to world-wide clinical diagnosis as indicated above. On the other hand analysis of mutations, deletions or insertions into specific viral gene products leading to expression of proteins with potential modified function may be of value for epidemiological and pathogenic studies and may have potential diagnostic relevance. For example EBV strain variation can be determined by analysing the sequence of especially the Epstein Barr Nuclear Antigen (EBNA)-2 and -3 genes, which contain specific sequences that allows differentiation into EBV strain types A and B, the B-strain being relatively more frequent in AIDS-associated lymphoma and in certain parts of the world. On the other hand, sequence variations (esp. point mutations and deletions) have been described for the EBNA-1, Latent Membrane Protein (LMP)-1, LMP-2 and ZEBRA encoding genes, of which the LMP-1 specific 30 bp deletion variant has been linked to a more aggressive oncogenic phenotype.

The availability of techniques to specifically analyse viral DNA and expressed RNA and protein are required for accurate diagnosis. One example of a technique for the amplification of a DNA target segment is the so-called "polymerase chain reaction" (PCR). PCR in combination with the proper primer sets is well suited for detection of viral DNA, whereas immunohistochemistry combined with appropriate antibody reagents is the method of choice for visualization of tumor associated viral proteins. High copy numbers of viral RNA can be detected by RNA in situ hybridization as routinely applied for the detection of EBER-1 and -2, which are expressed at extremely high copy numbers in virtually all EBV-associated tumors. The detection of low copy numbers of viral mRNA requires more sensitive techniques such as RT-PCR and Nucleic Acid Sequence Based Amplification (NASBA). Application of RT-PCR is seriously hampered by the need for spliced mRNA in order to allow viral gene expression in a viral DNA background therefore limiting its use to only a selected set of spliced viral genes. In addition, the need for high temperatures in the PCR part of the RT-PCR reaction seriously limits its application to in situ diagnostic approaches.

Another drawback of RT-PCR is the requirement of splice sites within the transcript of interest to exclude amplification of genomic DNA and the fact that it is a two-step reaction.

These limitations are overcome by using the NASBA approach for analysing viral mRNA expression both in tissue extracts and by in situ analysis at the single cell level. NASBA allows selective amplification of reading frame or exon-specific viral mRNA in a viral DNA background and allows visualizabon of (viral) mRNA expression in thin sections of tumor tissue without affecting cell morphology (in situ NASBA). As NASBA is not limited by the need for choosing specific primer sets spanning intron sequences, exon-specific primers and probes may be utilized. NASBA also allows more simple and broadly applicable analysis of genetic variations in expressed viral genes. Using NASBA, RNA but not genomic DNA is amplified independently of splice sites.

Based on their splicing patterns, four types of EBV transcripts can be distinguished:

Transcripts which are extensively spliced in the noncoding region but not in the coding region, like EBNA1 transcripts (Kerr et al., Virol; 187:189–201 (1992)).

Transcripts which are spliced in the coding domain, like LMP1 and LMP2 (Laux et al., J Gen Virol: 70: 3079–84 (1989)).

Transcripts which are not spliced at all, like the EBER1 and EBER2 transcripts (Clemens, Mol Biol Reports; 17: 81–92 (1993)).

Transcripts of which splicing patterns are not known. These are merely "early" transcripts, like BARF1 (Zhang et al., J Virol; 62(2):1862–9 (1988)), BDLF2 and BCRF1 (Vieira et al., PNAS; 88(4):1172–6 (1991)).

The present invention is related to the detection of a certain EBV mRNAs and provides oligonucleotides suitable for use in the amplification and subsequent detection of these mRNAs. The binding sites of the oligonucleotides according to the present invention are located in the following EBV genes:

Epstein Barr Early RNA 1 (EBER-1), Epstein Barr Nuclear Antigen 1 (EBNA-1), Latent Membrane Protein 1 (LMP-1), LMP-2, and vIL10 (BCRF-1). BARF1, and BDLF2 (all characterised by the nomenclature of Baer et al., Nature. vol., 310, pp 207–211, 1984).

An embodiment of the present invention is directed to oligonucleotides which are 10–35 nucleotides in length and comprise, at least a fragment of 10 nucleotides, of a sequence selected from the group consisting of:

EBNA-1, [the BKRF1reading frame spanning nucleotides 107950–109872],
EBER-1, [reading frame spanning nucleotides 6629–6795],
LMP-1, [the BNLF1 reading frame spanning nucleotides 169474–169207],
LMP-2, [exons 2, 3, 4, 5, 6, 7 and 8 spanning nucleotides 58–272, 360–458, 540–788, 871–951, 1026–1196, 1280–1495 and 1574–1682 respectively],
vIL10, [BCRF1 reading frame spanning nucleotides 8675–101841],
BARF1, [the reading frame spanning nucleotides 165504–166166], or
BDLF2, [the reading frame spanning nucleotides 132389–131130],
wherein all reading frame spanning nucleotide numbers are according to Baer et al., 1984.

Preferred oligonucleotides according to the present invention are 10–35 nucleotides in length and comprise, at least a fragment of 10 nucleotides, of a sequence selected from the group consisting of:

1.1, 5'-GCCGGTGTGTTGTTCGTATATGG-3' [SEQ.ID.NO.: 1],
1.2, 5'-CTCCCTTTACAACCTAAGGC-3' [SEQ.ID.NO.: 2],
2.1, 5'-AGAGACAAGGTCCTTAATCGCATCC-3' [SEQ.ID.NO.: 3], or
2.2, 5'-AATACAGACAATGGACTCCC-3' [SEQ.ID.NO.: 4], or its complementary sequence (EBNA-1), or
1.1, 5'-CGGGCGGACCAGCTGTACTTGA-3' [SEQ.ID.NO.: 6],
2.2, 5'-GAGGTTTTGATAGGGAGAGGAGA-3' [SEQ.ID.NO.: 7],
54, 5'-CGGACCACCAGCTGGTACTTGA-3' [SEQ.ID.NO.: 8],
55, 55'-GCTGCCCTAGAGGGTTTTGCTA-3' [SEQ.ID.NO.: 9], or
56, 5'-CGAGACGGCAGAAAGCAGA-3' [SEQ.ID.NO.: 10], or its complementary sequence (EBER-1), or
1.1, 5'-ATACCTAAGACAAGTTTGCT-3' [SEQ.ID.NO.: 12],
1.2, 5'-ATCAACCAATAGAGTCCACCA-3' [SEQ.ID.NO.: 13],
2.1, 5'-CATCGTTATGAGTGACTGGA-3' [SEQ.ID.NO.: 14], or
2.2, 5'-ACTGATGATCACCCTCCTGCTCA-3' [SEQ.ID.NO.: 15], or its complementary sequence (LMP-1), or
1.1, 5'-TAACTGTGGTTTCCATGACG-3" [SEQ.ID.NO.: 17],
1.2, 5'-AGGTACTCTTGGTGCAGCCC-3' [SEQ.ID.NO.: 18],
2.1, 5'-AGCATATAGGAACAGTCGTGCC-3' [SEQ.ID.NO.: 19], or
2.2, 5'-AGTGGACATGAAGAGCACGAA-3' [SEQ.ID.NO.: 20], or its complementary sequence (LMP-2), or
1.1, 5'-CAGGTTCATCGCTCAGCTCC-3' [SEQ.ID.NO.: 22],
1.2, 5'-GGCTGTCACCGCTTTCTTGG-3' [SEQ.ID.NO.: 23],
2.1, 5'-AGTGTTGGCACTTCTGTGG-3' [SEQ.ID.NO.: 24], or 2.2, 5'-AGCATGGGAGATGTTGGCAGC-3' [SEQ.ID.NO.: 25], or its complementary sequence (BARF-1), or
1.1, 5'-TGGAGCGAAGGTTAGTGGTC-3' [SEQ.ID.NO.: 27],
1.2, 5'-TACCTGGCACCTGAGTGTGGAG-3' [SEQ.ID.NO.: 28],
2.1, 5'-AGAATTGGATCATTTCTGACAGGG-3' [SEQ.ID.NO.: 29], or
2.2, 5'-AGACATGGTCTTTGGCTTCAGGGTC-3' [SEQ.ID.NO.: 30], or its complementary sequence (vIL10 (BCRF1)), or
1.1, 5'-CTACCTTCCACGACTTCACC-3' [SEQ.ID.NO.: 32],
1.2, 5'-AAGTCTTTTATAAGGCTCCGGC-3' [SEQ.ID.NO.: 33],
2.1, 5'-AGGCCATGGTGTCATCCATC3' [SEQ.ID.NO.: 34], or
2.2, 5'-AGAGAGAGAGTAGGTCCGCGG-3' [SEQ.ID.NO.: 35], or its complementary sequence (BDLF2).

A preferred embodiment of the present invention is directed to an oligonucleotide linked to a suitable promoter sequence.

A more preferred embodiment of the present invention is directed to a pair of oligonucleotides, for the amplification of a target sequence within a Epstein Barr virus sequence, for use as a set, comprising:
1.2, 5'-CTCCCTTTACAACCTAAGGC-3' [SEQ.ID.NO.: 2], and
2.1, 5'-AGAGACAAGGTCCTTAATCGCATCC-3' [SEQ.ID.NO.: 3] provided with a T7 polymerase promoter sequence 5'-aattctaatacgactcactataggg-3' [SEQ.ID.NO.: 37] (EBNA-1); or
1.1, 5'-CGGGCGGACCAGCTGTACTTGA-3' [SEQ.ID.NO.: 6] provided with a T7 polymerase promoter sequence 5'-aattctaatacgactcactataggg-3' [SEQ.ID.NO.: 37], and
2.2, 5'-GAGGTTTTGATAGGGAGAGGAGA-3' [SEQ.ID.NO.: 7] (EBER-1);
1.1, 5'-ATACCTAAGACAAGTTTGCT-3' [SEQ.ID.NO.: 12] provided with a T7 polymerase promoter sequence 5'-aattctaatacgactcactataggg-3'[SEQ.ID.NO.: 37], and
2.1, 5'-CATCGTTATGAGTGACTGGA-3' [SEQ.ID.NO.: 14] (LMP-1); or
1.2, 5'-aggtactcttggtgcagccc-3' [SEQ.ID.NO.: 18], and
2.1, 5'-agcatataggaacagtcgtgcc-3' [SEQ.ID.NO.: 19] provided with a T7 polymerase promoter sequence 5'-aattctaatacgactcactataggg-3' [SEQ.ID.NO.: 37] (LMP-2); or
1.2, 5'-ggctgtcaccgctttcttgg-3' [SEQ.ID.NO.: 23], and
2.1, 5'-agtgttggcacttctgtgg-3' [SEQ.ID.NO.: 24] provided with a T7 polymerase promoter sequence 5'-aattctaatacgactcactataggg-3' [SEQ.ID.NO.: 37] (BARF-1); or
1.1, 5'-TGGAGCGAAGGTTAGTGGTC-3' [SEQ.ID.NO.: 27], and
2.2, 5'-AGACATGGTCTTTGGCTTCAGGGTC-3' [SEQ.ID.NO.: 30] provided with a T7 polymerase promoter sequence 5'-aattctaatacgactcactataggg-3' [SEQ.ID.NO.: 37] (vIL10 (BCRF1)); or
1.1, 5'-CTACCTTCCACGACTTCACC-3' [SEQ.ID.NO.: 32] provided with a T7 polymerase promoter sequence 5'-aattctaatacgactcactataggg-3' [SEQ. ID.NO.: 37] and
2.1, 5'-AGGCCATGGTGTCATCCATC-3' [SEQ.ID.NO.: 34], or
2.2, 5'-AGAGAGAGAGTAGGTCCGCGG-3' [SEQ.ID.NO.: 35] (BDLF2).

The term "oligonucleotide" as used herein refers to a molecule comprised of two or more deoxyribonucleotides or ribonucleotides such as primers and probes.

The term "primer" as used herein refers to an oligonucleotide either naturally occurring (e.g. as a restriction fragment) or produced synthetically, which is capable of acting as a point of initiation of synthesis of a primer extension product which is complementary to a nucleic acid strand (template or target sequence) when placed under suitable conditions (e.g. buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least about 10 nucleotides in length of a sequence substantially complementary (P1) or homologous (P2) to the target sequence, but somewhat longer primers are preferred. Usually primers contain about 15–26 nucleotides but longer primers may also be employed.

Normally a set of primers will consist of at least two primers, one 'upstream' and one 'downstream' primer which together define the amplificate (the sequence that will be amplified using said primers).

The oligonucleotides according to the invention may also be linked to a promoter sequence. The term "promoter sequence" defines a region of a nucleic add sequence that is specifically recognized by an RNA polymerase that binds to a recognized sequence and initiates the process of transcription by which an RNA transcript is produced. In principle any promoter sequence may be employed for which there is a known and available polymerase that is capable of recognizing the initiation sequence. Known and useful promoters are those that are recognized by certain bacteriophage RNA polymerases such as bacteriophage T3, T7 or SP6.

It is understood that oligonucleotides consisting of the sequences of the present invention may contain minor deletions, additions and/or substitutions of nucleic acid bases, to the extent that such alterations do not negatively affect the yield or product obtained to a significant degree.

Another preferred embodiment of the present invention is directed to an oligonucleotides which are 10–35 nucleotides in length and comprise, at least a fragment of 10 nucleotides, of a sequence selected from the group consisting of:
5'-CGTCTCCCCTTTGGAATGGCCCCTGGACCC-3' [SEQ.ID.NO.: 5] (EBNA-1),
5'-GTACAAGTCCCGGGTGGTGAG-3' [SEQ.ID.NO.: 11] (EBER-1),
5'-GGACAGGCATTGTTCCTTGG-3' [SEQ.ID.NO.: 16] (LMP-1),
5'-AGCTCTGGCACTGCTAGCGTCACTGATTTT-3' [SEQ.ID.NO.: 21] (LMP-2),
5'-CTGGTTTAAACTGGGCCCAGGAGAGGAGCA-3' [SEQ.ID.NO.: 26] (BARF-1),
5'-CAGACCAATGTGACAATTTTCCCCAAATGT-3' [SEQ.ID.NO.: 31] (vIL10 (BCRF1)), or
5'-CCAATGGGGGAGGAGAGACCAAGACCAATA-3' [SEQ.ID.NO.: 36] (BDLF2),
provided with a detectable label. Said oligonucleotides may be used for the detection of the amplificate generated using the oligonucleotides according to the present invention. Probes comprising said sequence are also part of the present invention.

An oligonucleotide sequence used as detection-probe may be labeled with a detectable moiety. Various labeling moieties are known in the art. Said moiety may, for example, either be a radioactive compound, a detectable enzyme (e.g.

horse radish peroxidase (HRP)) or any other moiety capable of generating a detectable signal such as a colorimetric, fluorescent, chemiluminescent or electrochemiluminescent signal. Preferred analysis systems wherein said labels are used are electrochemiluminescence (ECL) based analysis or enzyme linked gel assay (ELGA) based analysis.

Another preferred embodiment of the present invention is directed to a method for the detection of EBV-specific RNA sequences in human tissue (extracts), peripheral blood and white blood cells, body fluids, tumor cell lines, etc. using the oligonucleotides according to the present invention. Said method comprising the following steps:

amplifying a target sequence within said mRNA using (a pair of oligonucleotides according to the invention and suitable amplification reagents, reacting the sample, optionally containing amplified nucleic acid, with an oligonucleotide according to the present invention as a detection-probe, detecting hybrids formed between the amplified sequence and the probe.

Various techniques for amplifying nucleic acid are known in the art. One example of a technique for the amplification of a DNA target segment is the so-called "polymerase chain reaction" (PCR). With the PCR technique the copy number of a particular target segment is increased exponentially with a number of cycles. A pair of primers is used and in each cycle a DNA primer is annealed to the 3' side of each of the two strands of the double stranded DNA-target sequence. The primers are extended with a DNA polymerase in the presence of the various mononucleotides to generate double stranded DNA again. The strands of the double stranded DNA are separated from each other by thermal denaturation and each strand serves as a template for primer annealing and subsequent elongation in a following cycle. The PCR method has been described in Saiki et al., Science 230, 135, 1985 and in European Patents no. EP 200362 and EP 201184.

Another technique for the amplification of nucleic acid is the so-called transcription based amplification system (TAS). The TAS method is described in International Patent Appl. no. WO 88/10315. Transcription based amplification techniques usually comprise treating target nucleic acid with two oligonucleotides one of which comprises a promoter sequence, to generate a template including a functional promoter. Multiple copies of RNA are transcribed form said template and can serve as a basis for further amplification.

An isothermal continuous transcription based amplification method is the so-called NASBA process ("NASBA") as described in European Patent no. EP 329822. NASBA includes the use of T7 RNA polymerase to transcribe multiple copies of RNA from a template including a T7 promoter.

For RNA amplification (as with the method according to the invention), the NASBA technology, or another transcription based amplification technique, is a preferred technology. If RT-PCR is used for the detection of viral transcripts differentiation of mRNA- and DNA-derived PCR products is necessary. For spliced transcripts, like the IEA mRNA, the exonintron structure can be used. However, mRNA species encoding the late structural proteins are almost elusively encoded by unspliced transcripts. DNAse treatment prior to RT-PCR can be employed (Bitsch, A. et al., J Infect. Dis 167, 740–743, 1993; Meyer, T. et al., Mol. Cell Probes. 8, 261–271, 1994), but sometimes fails to remove contaminating DNA sufficiently (Bitsch, A. et al., 1993).

In contrast to RT-PCR, NASBA, which is based on RNA transcription by T7 RNA polymerase (Kievits et al., J Virol Meth; 35:273–86), does not need differentiation between RNA- and DNA-derived amplification products since it only uses RNA as its principal target. NASBA enables specific amplification of RNA targets even in a background of DNA.

This method was used for the analysis of EBV transcripts in whole blood samples from HIV-infected individuals.

Test kits for the detection of EBV in clinical samples are also part of the present invention. A test kit according to the invention may comprise a pair of oligonucleotides according to the invention and a probe comprising an oligonucleotide according to the invention. Such a test kit may additionally comprise suitable amplification reagents such as DNA and or RNA polymerases and mononucleotides. Test kits that can be used with the method according to the invention may comprise the oligonucleotides according to the invention for the amplification and subsequent detection of EBV-specific RNA sequences.

The invention is further exemplified by the following examples.

EXAMPLES

Example 1

Selection and optimization of specific primer and probe sequences for the detection of EBNA-1 mRNA.

From a large panel of in vitro cultured BL and LCL cell lines obtained from different parts of the world and from fresh tumor biopsy specimens from a variety of EBV positive tumor tissues, the specific nucleotide sequence of the BKRF1 reading frame was determined and aligned with the prototype B95-8 sequence. Surprisingly, it became apparent from these data that the field isolates of EBV were rather more conserved when aligned with each other than when compared to the B95-8 sequence, making the latter rather a mutant strain. In addition, certain mutations were observed that were more common among NPC- and LCL's derived sequences obtained from SE-Asia, whereas other mutations were more common among LCL and BL-derived isolates from central Africa, indicative of regional strain differences. In the different LCL's analysed, B95-8 transformed lines could be clearly discriminated from LCL's derived from endogenous virus transformed (=spontaneous growing) lines.

These analyses also revealed specific areas within the BKRF1 sequence that were highly conserved among all isolates studied. These regions were utilized to search for sequences that could be applied for BKRF1 exon-specific and sensitive mRNA amplification using NASBA.

From a number of candidate sequences selected within the conserved regions of BKRF1, four primer sets and a corresponding detection probe were synthesized and utilized to determine the absolute and relative sensitivity of amplification using in vitro generated run-off transcripts and dilution series of EBV-genome positive B-cells (JY cells) made in a fixed number (n=50,000) of EBV-genome negative B-cells (BJAB or RAMOS cells).

In these experiments, using the 'standard' NASBA protocol (see below), it was found that the most sensitive and specific amplification of BKRF1-specific mRNA sequences could be achieved using the primers EBNA1–1.2 and -2.1, with SEQ.ID.No.: 2 and SEQ.ID.No.: 3, combined with the detection probe with SEQ.ID.No.: 5.

FIG. 1 illustrates the results of a typical NASBA reaction using two combinations of primer sets derived from the BKRF1 sequence. The primer combination (1.2 with 2.1), giving a specific amplification product of 203 bp, allows the detection of 10 EBV-infected JY cells in a background of 50.000 EBV-negative RAMOS cells.

'standard' NASBA Protocol:

EBV-positive and negative cells and/or tissue samples were routinely treated with NASBA lysis buffer as described elsewhere. NASBA reactions were carried out as described by Kievits et al., using 100 ng of total RNA per reaction (unless mentioned otherwise). Aqueous cell/tissue-derived RNA solutions were obtained with the silica-based isolation method (Boom et al. European Patent No. 0389063 B1: U.S. Pat. No. 5,234,809) and used directly in the NASBA reaction. Isopropanol precipitates of EBER1-RNA as obtained by the RNAzol method (Cinna Biotex) were centrifuged in an Eppendorf centrifuge at 14.000 rpm for 30 minutes. The RNA pellet was washed with 70% ethanol, dried under vacuum for 10–15 minutes and dissolved in RNAse-free water. Five micoliters (µl) of each sample was mixed with 4 µl of 5×NN buffer (200 mM Tris pH8.5, 60 mM MgCl2, 350 mM Kcl, 20 mM DTT, 5 mM of each dNTP, 10 mM rATP, rUTP, rCTP and 7.5 mMrGTP, 2.5 mM ITP), 4 µl primer mix (1 µM of each primer in 75% DMSO), and 2 µl RNAse-free water. The samples were heated to 65° C. for 5 minutes, allowed to cool down to 41° C. after which 5 µl of enzyme mix (6.5 mM sorbitol,3,4 µgBSA, 0.08U RNAsaH (Pharmacia), 32.0 U T7 RNA polymerase (Pharmacia) and 6.44 U AMV-RT (Pharmacia)). The reaction was incubated at 41° C. for 90 minutes. Reaction products were evaluated by gelelectrophoresis using 1.5% agarose in TBE. NASBA products were transferred from the gels to nylon filters (Quiabrane, Quiagen, Chatsworth, Calif., USA) via capillary blotting in 10×SSC and hybridized to specific $\gamma^{32}P$ end-labeled oligonucleotide probes using standard procedures. Radioactivity was detected using Kodak XAR-1 film.

Example 2

Detection of additional EBV RNA targets using optimized primer sets.

Similarly, sequence comparison and primer optimization studies allowed the selection of specific sets of reagents for the detection of EBV-encoded mRNA for LMP-1, LMP-2, EBER-1 and other EBV gene targets. For some targets the results are shown in FIG. 2, panels A–D.

FIG. 2 panels A and B shows the results of NASBA reactions for LMP-1 and LMP-2 on dilution series of EBV-positive JY cells in 50.000 EBV-negative RAMOS cells as described for EBNA1.

The data indicate that LMP-1 specific primerset 1.1 (SEQ.ID.No.: 12) combined with 2.1 (SEQ.ID.No.: 14), giving a product of 248 bp, allows the detection of mRNA equivalent to 1–10 JY cells in a background of 50.000 EBV-negative RAMOS cells. The LMP-2 set 1.2 (SEQ.ID.No.: 18) combined with 2.1 (SEQ.ID.No.: 19), giving a product of 196 bp, allows the clear detection of 1 JY cell in the presence of 50,000 RAMOS cells, which is slightly better than the combination of LMP-2 set 1.1 (SEQ.ID.No.: 17) with 2.2 (SEQ.ID.No.: 20), giving a product of 226 bp.

FIG. 2 panel C shows the results of NASBA assays to determine the analytical sensitivity of EBER-1. These results show that the primer combination EBER 1.1 (SEQ. ID.No.: 6) with 2.2 (SEQ.ID.No.: 7), giving a product of 140 bp, allows the detection of 100 RNA molecules using in vitro generated RNA run-off transcripts.

FIG. 2 panel D shows the results of EBER1 NASBA with RNA isolated from a dilution series of JY cells in 50.000 RAMOS cells, indicating that about 100 JY cell equivalents can be detected. Due to the loss of small sized RNA molecules during the silica isolation procedure, insensitivity is detected.

Example 3

Optimization of EBV-RNA isolation and NASBA reaction conditions.

Optimization of RNA isolation method or NASBA reaction conditions, such as concentration of DMSO, KCl or Betaine (N,N,N-trimethylglycine) may improve the sensitivity of detection of EBV-specific RMA without affecting its specificity.

FIG. 3A shows the comparison of two RNA isolation methods for the isolation of the small molecular weight EBER1 RNA's, which are present at high abundance in EBV-transformed cells like JY, but which are not isolated with high efficiency by the silica method of Boom et al. Standardized quantifies of in vitro generated 170 bp run-off transcripts were used as input for RNA isolation using the RNAzol (Cinna Biotex) and Boom isolation methods. Isolated RNA was used as input for NASBA with primers 1.1 (SEQ.ID.No.: 6) and 2.2 (SEQ.ID.No.: 7) giving a product of 140 bp. The results show that the RNAzol method results in a 10–100 fold more efficient extraction level of this small EBER1 RNA The RNAzol method is more efficient in isolating the small EBER1 molecules compared to the Boom method although this does not apply for RNA molecules exceeding 500 bp (data not shown).

In addition the efficiency of amplification of specific RNA during NASBA may be improved by the addition of chemical substances, either to improve the processivity of the enzymes involved (KCl or MgCl2) or to decrease the formation of secondary structures in the amplified and target RNA (Betain or DMSO).

FIG. 3B shows the influence of variation in KCl -concentration as applied to the specific detection of EBV-specific BDLF2 RNA transcripts in standardized RNA extracts of 100 JY cells in 50.000 RAMOS cells. Concentrations of KCl , between 40–60 mM are optimal for this transcript (FIG. 3B) whereas for most other targets this was 60–70 mM.

Furthermore, as shown in FIG. 3C, the addition of betain up to 600 mM to the NASBA reaction mix greatly improved the detection of EBV-specific RNA from the BCRF1 gene, encoding the viral homologue of IL10 (v-IL10) which shows significant secondary structure formation (data not shown). In this case the RNA was isolated from 30 mM butyrate-induced EBV-positive RAJI-cells.

Example 4

Application of NASBA for the detection of EBV mRNA expression in human tumor biopsy specimens.

As in healthy EBV-carrying individuals EBV-DNA may be present in latently infected circulating and tissue-infiltrating B-cells and in virions secreted in body fluids by sporadic virus-producing B- or epithelial cells, the detection of virus-specific RNA, related to the different EBV-latency programs may provide a means of diagnosing aberrant viral activity in the host, linked to tumor formation. The level of viral RNA transcripts in tissues and body fluids of healthy carriers is considered to be too low for detection without purification of B-cells as only 1 in $10^5$–$10^6$ B-cells is estimated to harbour EBV in these cases. Therefore the detection of viral RNA in non-purified cells or tissues is considered to be of diagnostic and prognostic value in cases of suspected EBV-associated (malignant) diseases. NASBA provides an excellent and unique tool for analysis of viral transcriptional activity in human material as it allows direct detection of any viral RNA species not influenced by the presence of the viral. DNA genome. As EBNA1 is considered to be expressed in all stages of EBV-infection its detection would be a direct reflection of viral presence and transcriptional activity. From a series of EBV-positive and -negative frozen tumor biopsies 4 micron sections were cut and directly treated with NASBA lysis buffer to release the nucleic acids, which were further isolated on silica beads.

The quality of isolated RNA was checked by detection of 18S/28S ribosomal RNA bands after electrophoresis in 1% agarose and further analysed for the presence of U1A mRNA encoding the constitutively expressed human snRNP protein U1A. EBV-EBNA1 mRNA was detected by NASBA using BKRF1-specific primer set 1.2 and 2.1 as described in FIG. 1 and by RT-PCR using specific primers located around the Q/U/K spice site as reported elsewhere. The results of this analysis are listed in Table 1 which clearly show that NASBA allows the specific detection of EBNA-1 mRNA sequences in EBV-positive human tumor tissue-derived extracts, with greater sensitivity than RT-PCR and even allows detection in samples with inferior RNA quality or with RT-PCR inhibitory agents.

In a second series of experiments the presence of EBV-EBNA1 RNA was analysed in cervical scrapes collected for detection of human Papillomaviruses, some of which contained EBV-DNA as determined by EBV-DNA PCR using primers derived from the BAM-W region. The presence and quality of host cell RNA was checked as indicated above. Results are indicated in Table 2, showing that no EBV-RNA was detected in these samples despite the presence of HPV-DNA (not shown) and EBV-DNA. This demonstrates the specificity of EBV-NASBA.

Example 5

NASBA-mediated detection and differentiation of EBV specific RNA transcription in Nasopharyngeal Carcinoma (NPC) and Hodgkin's Disease (HD).

As EBV-associated malignancies are characterised by distinct patterns of viral gene transcription, associated with but not limited to the known latency programs, the differential analysis of viral transcriptional activity in human tissue or body fluids may be of diagnostic importance. As indicated in FIG. 5, NASBA provides an excellent tool for this purpose as demonstrated in this example by the differential detection of viral transcripts derived from the BARF1 and LMP2 genes.

For the detection and analysis of EBV-specific gene transcription in different human tumors, tissue RNA was extracted from 4 µm thin slices of frozen tumor material dissolved in NASBA lysis buffer using the Boom method.

FIGS. 4A and 4B show the results for the detection of virus-specific RNA derived from the BARF1 and LMP2 genes respectively, using primer combinations BARF1–1.2 (SEQ.ID.No.: 23) plus BARF1–2.1 (SEQ.ID.No.: 24) which yield a 252 bp product detectable by a BARF1-specific $\gamma^{32}$P-labeled probe (SEQ.ID.No.: 26) and combinations LMP2–1.2 (SEQ.ID.No.: 18) and LMP1–2.1 (SEQ.ID.No.: 19), yielding a 196 bp product as shown in FIG. 2. The results indicate that BARF1 transcription is specific for NPC and not detectable in HD, whereas the LMP2 gene is transcribed in both types of tumors.

These results illustrate the use of NASBA analysis in the specific detection and differentiation of EBV transcriptional activity in human biopsy material obtained from patients with different EBV-associated malignancies.

Example 6

In situ NASBA for detection of specific gene expression at the single cell level.

As EBV-gene transcription may vary in individual tumor cells and may be different in tumor infiltrating B-cells and differentiating epithelial cells compared to the surrounding malignant cells in human tissue samples, it is of importance to analyse EBV-gene expression at the single cell level.

In addition, the analysis of virus-induced host-specific gene expression in infected (transformed) cells but also in the surrounding normal tissues and tumor-infiltrating lymphocytes may be of relevance for understanding viral pathogenesis and host responses to the virus. Analysis of gene transcripts in cellular extracts does not provide information at the single cell level and (RT-)PCR techniques mostly are not very compatible with preservation of cell morphology required for histological examination.

NASBA, by virtue of its lack of high temperature cycling, does not destroy tissue and cell morphology during the amplification reaction and therefore is highly suited for in situ detection of low abundant viral and host cell transcripts and for gene expression related to synthesis of secreted host and viral products that elude immunocytochemical detection.

Example 7

EBV-specific BARF1-RNA as marker for EBV-associated Carcinomas.

EBV-associated malignancies are characterised by distinct patterns of viral gene transcription, associated with different latency programs indicated before.

Differential diagnosis using pattern analysis of viral transcriptional activity in human tissue or body fluids is of clinical-diagnostic importance.

The differentiation between lymphoma and aggressive lymphocyte-rich epithelial malignancies such as Gastric cancer (GC), Nasopharyngeal Carcinoma (NPC), also called epitheliomas is of dear importance in view of the therapeutic options.

The availability of a specific marker for the epithelial life of EBV would be of obvious benefit As shown in FIG. 6, the transcription of BARF1-RNA is specifically detected in Gastric cancer (GC). Nasopharyngeal Carcinoma (NPC) but not in EBV-positive Hodgkin's Disease (HD) and T-cell non-Hodgkin Lymphoma's (T-NHL) or control tissues.

BARF1-transcription therefore provides a specific marker for the differential diagnosis of epithelial malignancies associated with EBV.

NASBA provides an excellent tool for this purpose as demonstrated in this example.

For the detection and analysis of EBV-specific gene transcription in different human tumors, RNA was extracted from 10 µm slices of frozen tumor material dissolved in NASBA lysis buffer using the silica-based Boom method.

FIG. 6 shows the results for NASBA-mediated detection of virus-specific RNA derived from the BARF1 gene, using primer combinations BARF1–1.2 (SEQ.ID.NO 23) plus BARF1–2.1 (Seq.ID 24), which yield a 252 bp product detectable by a BARF1-specific $\gamma^{32}$P-labeled probe (Seq.ID 26).

The positive control (+con) contains RNA from the EBV-negative Louckes Burkitt Lymphoma cell line stably transfected with the BARF1-gene.

The negative control (−con) consists of RNA isolated from EBV negative Gastric Carcinoma. Also RNA from the EBV-negative B-cell line RAMOS is included as specificity control. The lanes marked HD and T-NHL represents BARF1 analysis with RNA isolated form EBV-positive Hodgkin Lymphoma (HD) and EBV-positive T-cell non-Hodgkin Lymphoma (T-NHL) respectively, which both showed EBV-specific EBER RISH and LMP1-protein by in situ staining and EBNA1, LMP1 and LMP2 RNA expression by NASBA on the same extracted RNA sample.

The Nasopharyngeal Carcinoma (NPC) and both Gastric Carcinoma (GC) samples were EBV-positive by EBER RISH analysis on frozen tissue sections.

All samples had good quality RNA as defined by a positive U1A RNA reaction.

The results indicate that BARF1 transcription is specific for NPC and GC and is not detectable in EBV+HD and T-NHL Figures:

The patent or application file contains at least one drawing executed in color. Copies of this patent or patent application publication with color drawing(s) will be provided by the Office upon request and payment of the necessary fee.

FIG. 1. illustrates the results of a typical NASBA reaction using two combinations of primer sets derived from the BKRF1 sequence.

FIG. 2.

panels A and B shows the results of NASBA reactions for LMP-1 and LMP-2 on dilution series of EBV-positive JY cells in 50.000 EBV-negative RAMOS cells as described for EBNA1.

panel C shows the results of NASBA assays to determine the analytical sensitivity of EBER-1.

panel D shows the results of EBER1 NASBA with RNA isolated from a dilution series of JY cells in 50.000 RAMOS cells, indicating that about 100 JY cell equivalents can be detected.

FIG. 3A. shows the comparison of two RNA isolation methods for the isolation of the small molecular weight EBER1 RNA's.

FIG. 3B. shows the influence of variation in KCl-concentration as applied to the specific detection of EBV-specific BDLF2 RNA transcripts FIG. 3C. shows the influence of addition of betain to the NASBA reaction mix as applied to the specific detection of EBV-specific BCRF1 RNA transcripts.

SEQUENCE LISTING

<160> NUMBER OF SEQ ID NOS: 37

Figure 1:
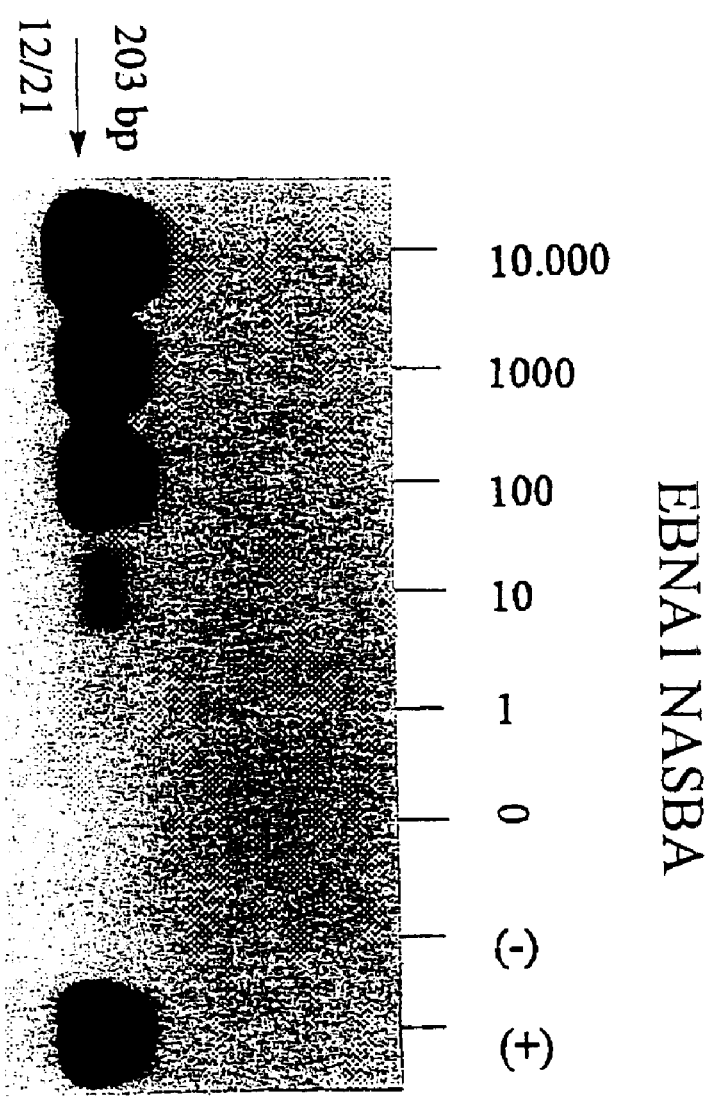
Figure 2A:
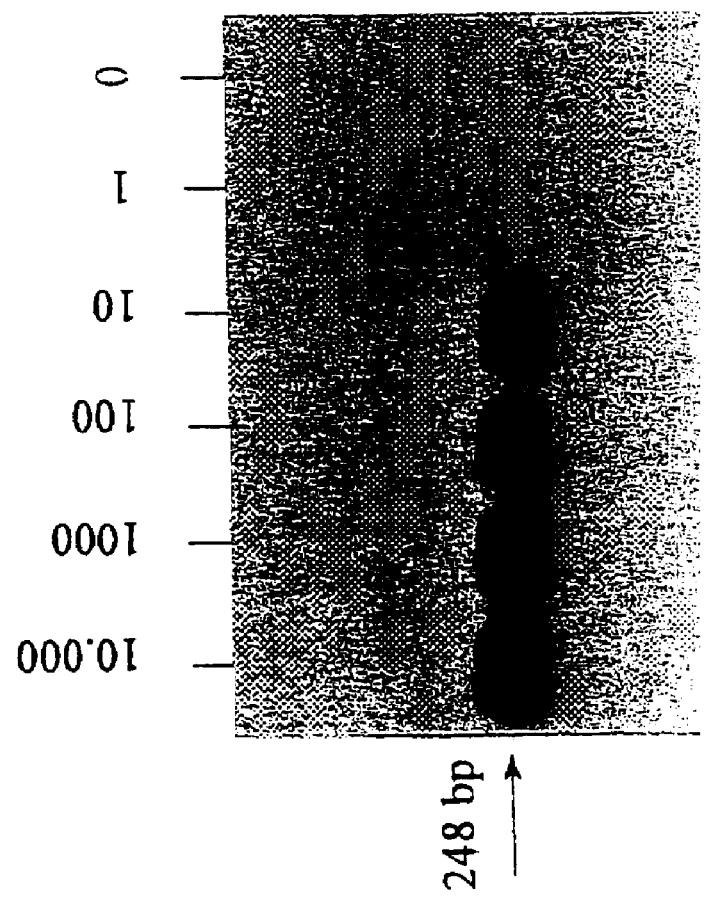
Figure 2B:
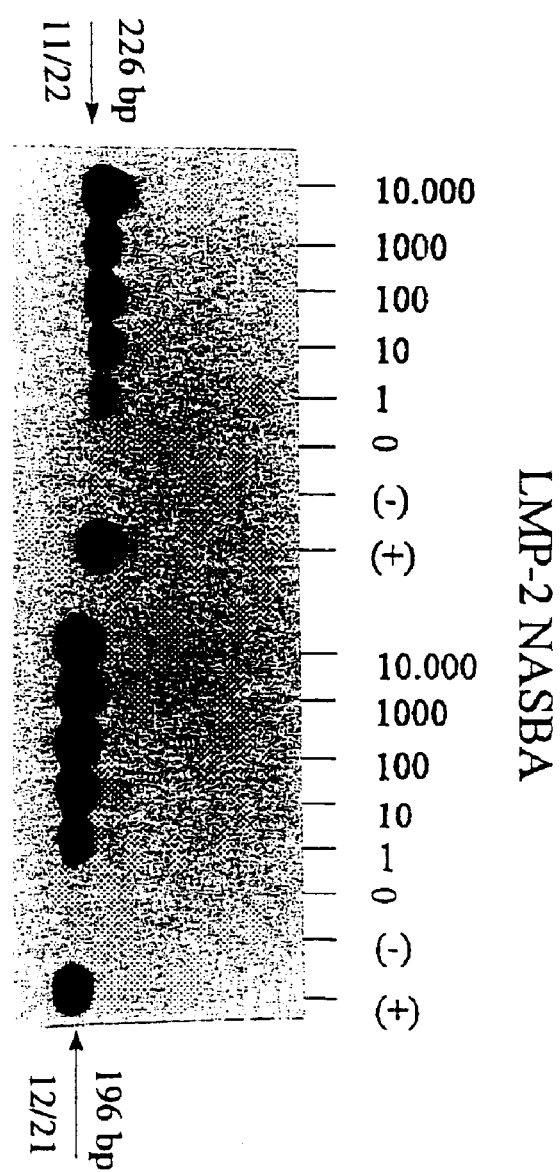
Figure 2C:
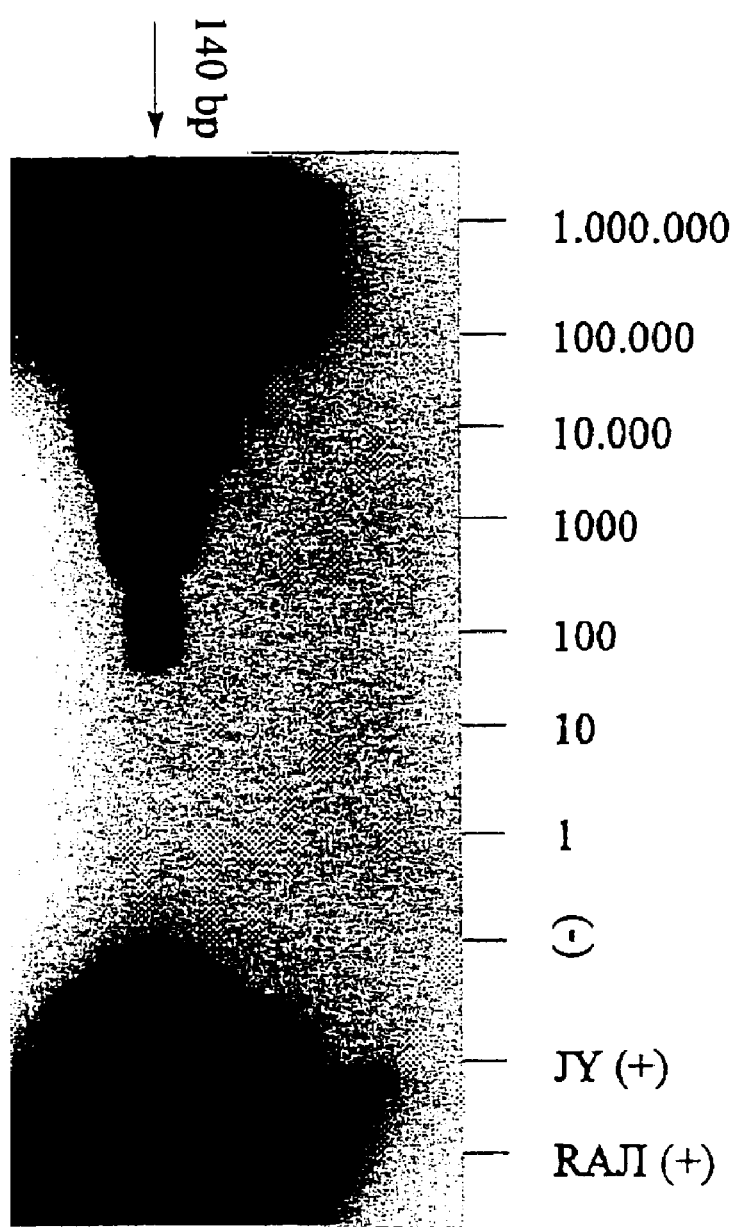
Figure 2D:
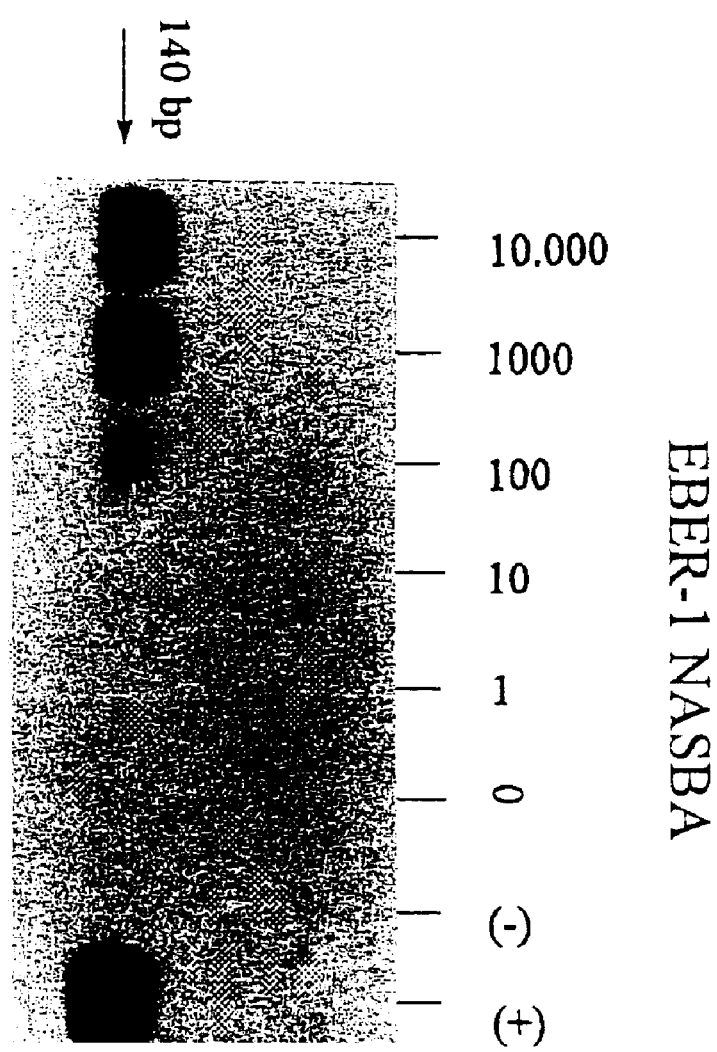
Figure 3A:
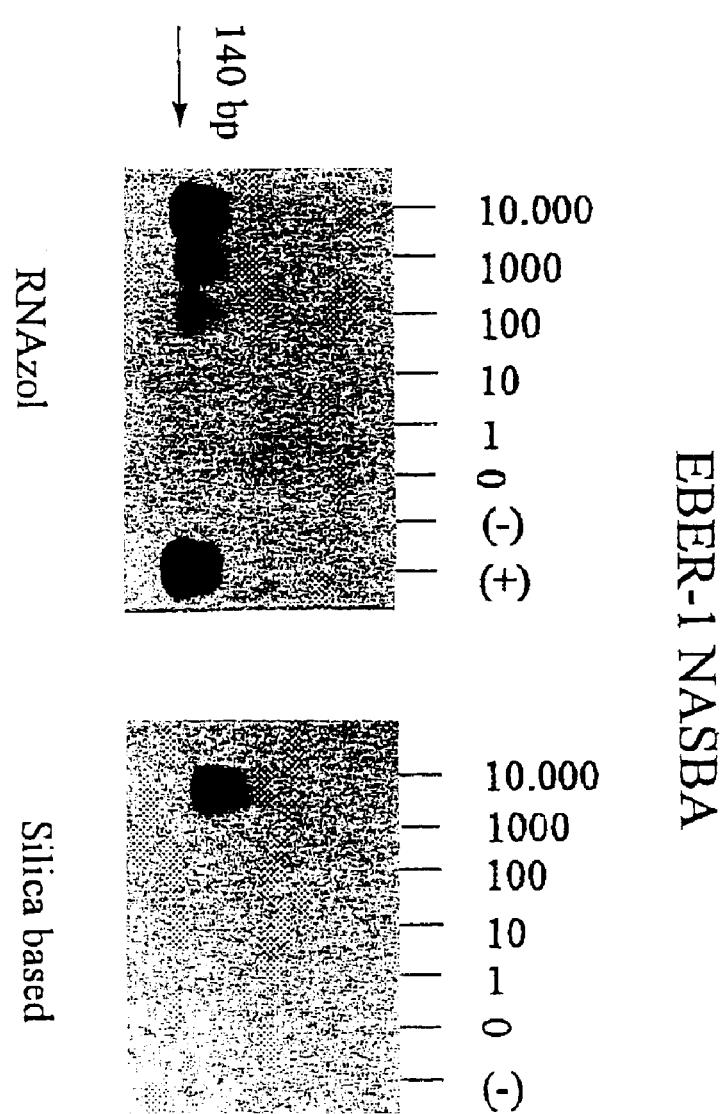
Figure 3B:
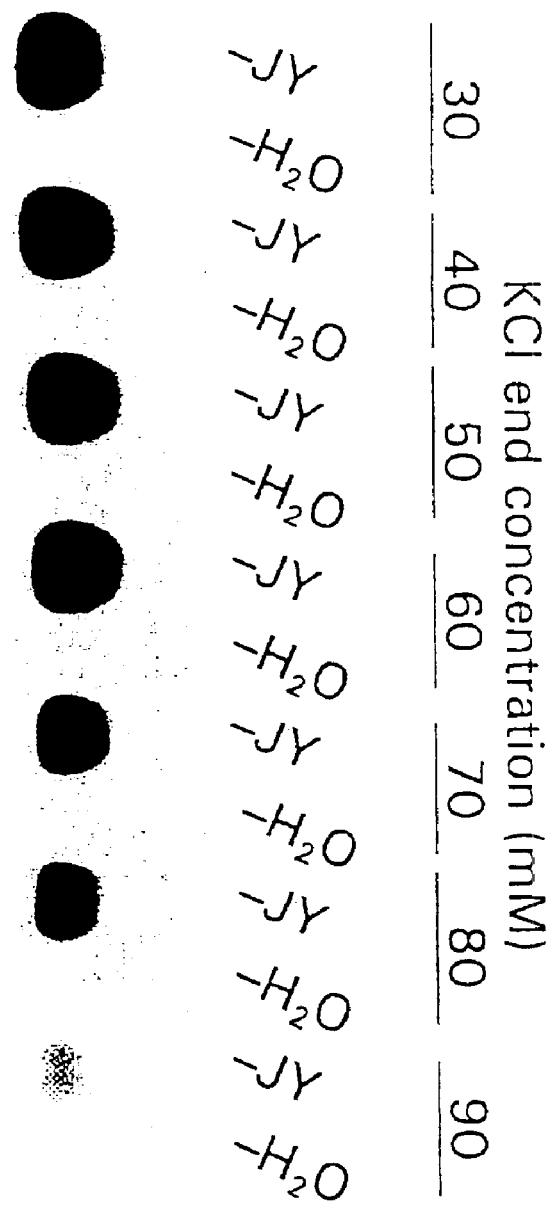
Figure 4A:
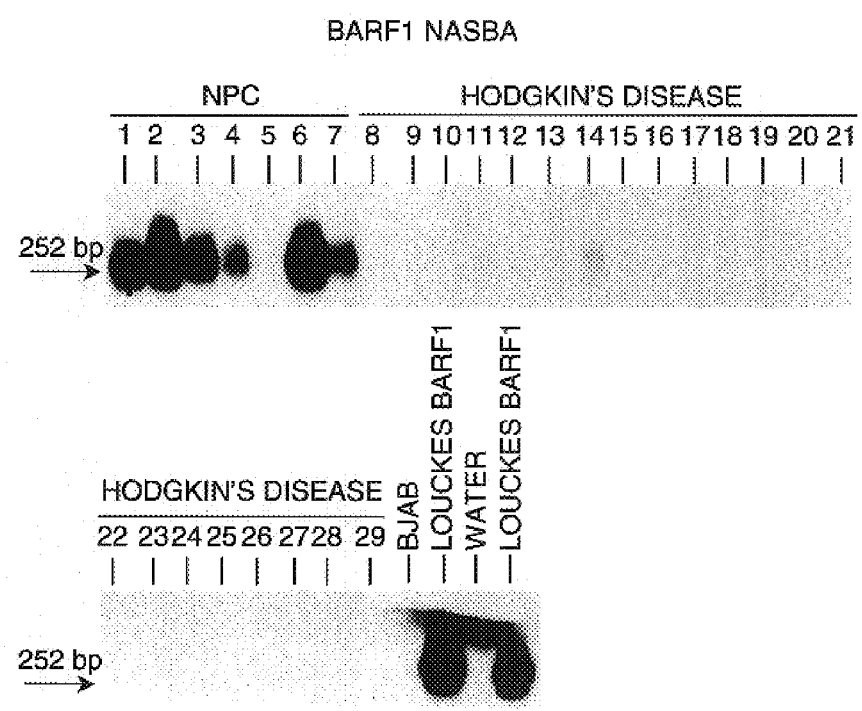
FIG. 4A and 4B show the results for the detection of virus-specific RNA derived from the BARF1 and LMP2 genes respectively.
Figure 4B:
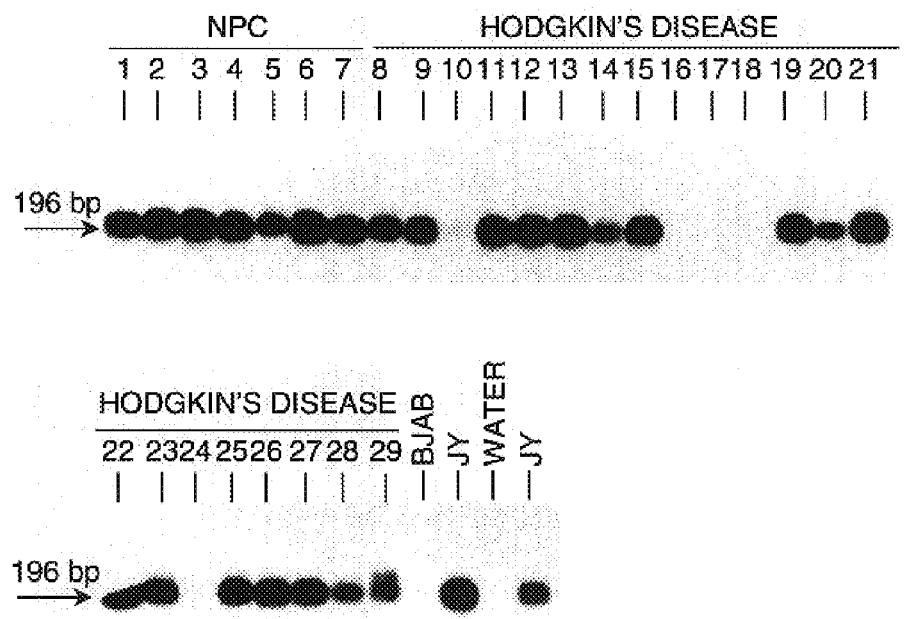
Figure 5:
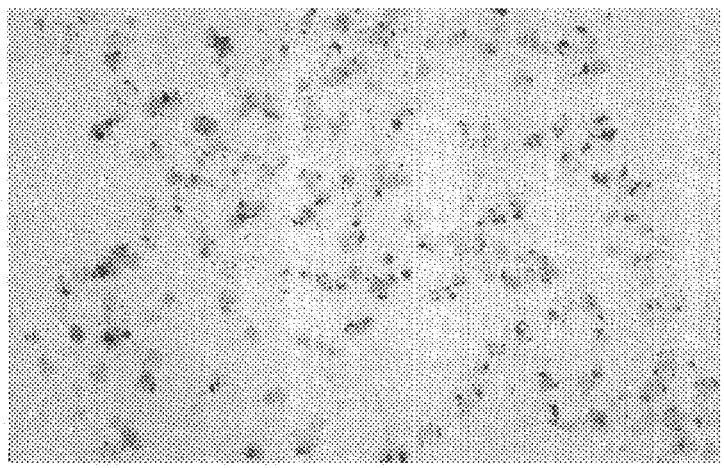
FIG. 5 shows the result of in situ NASBA detection of LMP2-specific gene expression in JY cells, prepared in agarose, fixed with formalin and embedded in parafin using standard histologic procedures.
Figure 6:
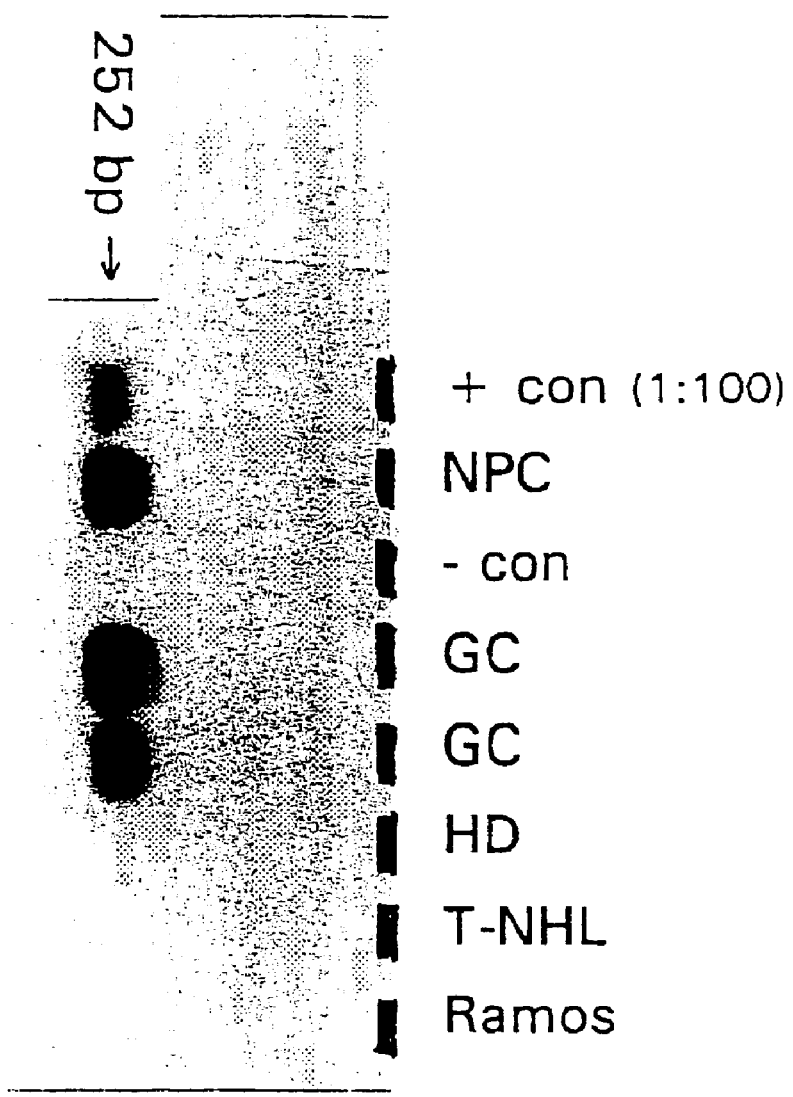
FIG. 6 shows the results for NASBA-mediated detection of virus-specific RNA derived from the BARF1 gene, using primer combinations BARF1–1.2 (Seq.ID 23) plus BARF1–2.1 (Seq.ID 24), which yield a 252 bp product detectable by a BARF1-specific $\gamma^{32}$P-labeled probe Seq.ID 26).

<210> SEQ ID NO 1
<211> LENGTH: 23
<212> TYPE: DNA
<213> ORGANISM: Epstein-Barr Virus

<400> SEQUENCE: 1
gccggtgtgt tgttcgtata tgg                    23

<210> SEQ ID NO 2
<211> LENGTH: 20
<212> TYPE: DNA
<213> ORGANISM: Epstein-Barr Virus

<400> SEQUENCE: 2
ctccctttac aacctaaggc                        20

<210> SEQ ID NO 3
<211> LENGTH: 25
<212> TYPE: DNA
<213> ORGANISM: Epstein-Barr Virus

<400> SEQUENCE: 3
agagacaagg tccttaatcg catcc                  25

<210> SEQ ID NO 4
<211> LENGTH: 20
<212> TYPE: DNA
<213> ORGANISM: Epstein-Barr Virus

<400> SEQUENCE: 4
aatacagaca atggactccc                                               20

<210> SEQ ID NO 5
<211> LENGTH: 30
<212> TYPE: DNA
<213> ORGANISM: Epstein-Barr Virus

<400> SEQUENCE: 5
cgtctcccct ttggaatggc ccctggaccc                                    30

<210> SEQ ID NO 6
<211> LENGTH: 22
<212> TYPE: DNA
<213> ORGANISM: Epstein-Barr Virus

<400> SEQUENCE: 6
cgggcggacc agctgtactt ga                                            22

<210> SEQ ID NO 7
<211> LENGTH: 23
<212> TYPE: DNA
<213> ORGANISM: Epstein-Barr Virus

<400> SEQUENCE: 7
gaggttttga tagggagagg aga                                           23

<210> SEQ ID NO 8
<211> LENGTH: 22
<212> TYPE: DNA
<213> ORGANISM: Epstein-Barr Virus

<400> SEQUENCE: 8
cggaccacca gctggtactt ga                                            22

<210> SEQ ID NO 9
<211> LENGTH: 22
<212> TYPE: DNA
<213> ORGANISM: Epstein-Barr Virus

<400> SEQUENCE: 9
gctgccctag agggttttgc ta                                            22

<210> SEQ ID NO 10
<211> LENGTH: 19
<212> TYPE: DNA
<213> ORGANISM: Epstein-Barr Virus

<400> SEQUENCE: 10
cgagacggca gaaagcaga                                                19

<210> SEQ ID NO 11
<211> LENGTH: 21
<212> TYPE: DNA
<213> ORGANISM: Epstein-Barr Virus

<400> SEQUENCE: 11
gtacaagtcc cgggtggtga g                                             21

<210> SEQ ID NO 12
<211> LENGTH: 20
<212> TYPE: DNA
<213> ORGANISM: Epstein-Barr Virus -continued

```
<400> SEQUENCE: 12
atacctaaga caagtttgct                                              20

<210> SEQ ID NO 13
<211> LENGTH: 21
<212> TYPE: DNA
<213> ORGANISM: Epstein-Barr Virus

<400> SEQUENCE: 13
atcaaccaat agagtccacc a                                            21

<210> SEQ ID NO 14
<211> LENGTH: 20
<212> TYPE: DNA
<213> ORGANISM: Epstein-Barr Virus

<400> SEQUENCE: 14
catcgttatg agtgactgga                                              20

<210> SEQ ID NO 15
<211> LENGTH: 23
<212> TYPE: DNA
<213> ORGANISM: Epstein-Barr Virus

<400> SEQUENCE: 15
actgatgatc accctcctgc tca                                          23

<210> SEQ ID NO 16
<211> LENGTH: 20
<212> TYPE: DNA
<213> ORGANISM: Epstein-Barr Virus

<400> SEQUENCE: 16
ggacaggcat tgttccttgg                                              20

<210> SEQ ID NO 17
<211> LENGTH: 20
<212> TYPE: DNA
<213> ORGANISM: Epstein-Barr Virus

<400> SEQUENCE: 17
taactgtggt ttccatgacg                                              20

<210> SEQ ID NO 18
<211> LENGTH: 20
<212> TYPE: DNA
<213> ORGANISM: Epstein-Barr Virus

<400> SEQUENCE: 18
aggtactctt ggtgcagccc                                              20

<210> SEQ ID NO 19
<211> LENGTH: 22
<212> TYPE: DNA
<213> ORGANISM: Epstein-Barr Virus

<400> SEQUENCE: 19
agcatatagg aacagtcgtg cc                                           22

<210> SEQ ID NO 20
<211> LENGTH: 21
<212> TYPE: DNA
<213> ORGANISM: Epstein-Barr Virus
```

-continued

```
<400> SEQUENCE: 20
agtggacatg aagagcacga a                                           21

<210> SEQ ID NO 21
<211> LENGTH: 30
<212> TYPE: DNA
<213> ORGANISM: Epstein-Barr Virus

<400> SEQUENCE: 21
agctctggca ctgctagcgt cactgatttt                                  30

<210> SEQ ID NO 22
<211> LENGTH: 20
<212> TYPE: DNA
<213> ORGANISM: Epstein-Barr Virus

<400> SEQUENCE: 22
caggttcatc gctcagctcc                                             20

<210> SEQ ID NO 23
<211> LENGTH: 20
<212> TYPE: DNA
<213> ORGANISM: Epstein-Barr Virus

<400> SEQUENCE: 23
ggctgtcacc gctttcttgg                                             20

<210> SEQ ID NO 24
<211> LENGTH: 19
<212> TYPE: DNA
<213> ORGANISM: Epstein-Barr Virus

<400> SEQUENCE: 24
agtgttggca cttctgtgg                                              19

<210> SEQ ID NO 25
<211> LENGTH: 21
<212> TYPE: DNA
<213> ORGANISM: Epstein-Barr Virus

<400> SEQUENCE: 25
agcatgggag atgttggcag c                                           21

<210> SEQ ID NO 26
<211> LENGTH: 30
<212> TYPE: DNA
<213> ORGANISM: Epstein-Barr Virus

<400> SEQUENCE: 26
ctggtttaaa ctgggcccag gagaggagca                                  30

<210> SEQ ID NO 27
<211> LENGTH: 20
<212> TYPE: DNA
<213> ORGANISM: Epstein-Barr Virus

<400> SEQUENCE: 27
tggagcgaag gttagtggtc                                             20

<210> SEQ ID NO 28
<211> LENGTH: 22
<212> TYPE: DNA
```

-continued

<213> ORGANISM: Epstein-Barr Virus

<400> SEQUENCE: 28
tacctggcac ctgagtgtgg ag                                        22

<210> SEQ ID NO 29
<211> LENGTH: 24
<212> TYPE: DNA
<213> ORGANISM: Epstein-Barr Virus

<400> SEQUENCE: 29
agaattggat catttctgac aggg                                      24

<210> SEQ ID NO 30
<211> LENGTH: 25
<212> TYPE: DNA
<213> ORGANISM: Epstein-Barr Virus

<400> SEQUENCE: 30
agacatggtc tttggcttca gggtc                                     25

<210> SEQ ID NO 31
<211> LENGTH: 30
<212> TYPE: DNA
<213> ORGANISM: Epstein-Barr Virus

<400> SEQUENCE: 31
cagaccaatg tgacaatttt ccccaaatgt                                30

<210> SEQ ID NO 32
<211> LENGTH: 20
<212> TYPE: DNA
<213> ORGANISM: Epstein-Barr Virus

<400> SEQUENCE: 32
ctaccttcca cgacttcacc                                           20

<210> SEQ ID NO 33
<211> LENGTH: 22
<212> TYPE: DNA
<213> ORGANISM: Epstein-Barr Virus

<400> SEQUENCE: 33
aagtctttta taaggctccg gc                                        22

<210> SEQ ID NO 34
<211> LENGTH: 20
<212> TYPE: DNA
<213> ORGANISM: Epstein-Barr Virus

<400> SEQUENCE: 34
aggccatggt gtcatccatc                                           20

<210> SEQ ID NO 35
<211> LENGTH: 21
<212> TYPE: DNA
<213> ORGANISM: Epstein-Barr Virus

<400> SEQUENCE: 35
agagagagag taggtccgcg g                                         21

<210> SEQ ID NO 36
<211> LENGTH: 30

-continued

```
<212> TYPE: DNA
<213> ORGANISM: Epstein-Barr Virus

<400> SEQUENCE: 36 ccaatgggg aggagagacc aagaccaata                                    30

<210> SEQ ID NO 37
<211> LENGTH: 25
<212> TYPE: DNA
<213> ORGANISM: Artificial sequence
<220> FEATURE:
<223> OTHER INFORMATION: T7 polymerase promoter sequence

<400> SEQUENCE: 37
aattctaata cgactcacta taggg                                        25
```

What is claimed is:

1. A method for determining the presence of EBV-positive nasopharyngeal carcinoma or gastric carcinoma cells in a sample of an individual suspected of or at risk for carrying an EBV associated disease, comprising:
   (a) amplifying one or more targets from the BKRF1 reading frame spanning nucleotides 107950–109872 of EBNA-1,
   (b) amplifying one or more target sequence(s) selected from the BARF1 reading frame spanning nucleotides 165504–166166,
   (c) detecting the presence or absence of the amplified target sequences of steps (a) and (b), and
   (d) determining the presence of EBV-positive nasopharyngeal carcinoma or gastric carcinoma cells from the presence of the amplified target sequences of steps (a) and (b).

2. The method according to claim 1 wherein
   the step of amplifying the BKRF1 reading fame in step (a) is performed using a pair of oligonucleotides, each oligonucleotide comprising a sequence specific for EBNA-1, the EBNA-1 specific sequences consisting of 5'-CTCCCTTTACAACCTAAGGC-3' [SEQ.ID.NO.: 2], and
   5'-AGAGACAAGGTCCTTAATCGCATCC-3' [SEQ.ID.NO.: 3],
      wherein the latter oligonucleotide further comprises a T7 polymerase promoter sequence 5'-aattctaatacgactcactataggg-3' (SEQ ID NO:37); and
   and a pair of oligonucleotides specific for EBER-1 consisting of 1.1, 5'-CGGGCGGACCAGCTGTACTTGA-3' [SEQ.ID.NO.: 6] provided with a T7 polymerase promoter sequence 5'-aattctaatacgactcactatagg-3', and the step of amplifying the BARF1 reading frame in step (b) is performed using a pair of oligonucleotides, each oligonucleotide comprising a sequence specific for BARF-1, the BARF-1 specific sequences consisting of 5'-GGCTGTCACCGCTTTCTTGG-3' [SEQ.ID.NO.: 23], and
   5'-AGTGTTGGCACTTCTGTGG-3' [SEQ.ID.NO.: 24],
      wherein the latter oligonucleotide further comprises a T7 polymerase promoter sequence 5'-aattctaatacgactcactataggg-3' (SEQ ID NO:37).

3. The method according to claim 1, wherein the RNA is amplified using a transcription based amplification technique.

4. The method according to claim 3, wherein said amplification technique is NASBA.

5. The method according to claim 1, further comprising detecting the presence or absence of the amplified target sequence of (a).

* * * * *